(12) United States Patent
Orangi et al.

(10) Patent No.: US 12,259,349 B2
(45) Date of Patent: Mar. 25, 2025

(54) SOIL MOISTURE ESTIMATION

(71) Applicant: The University of Melbourne, Melbourne (AU)

(72) Inventors: Amir Orangi, Melbourne (AU); Guillermo Andres Narsilio Ferrero, Melbourne (AU)

(73) Assignee: The University of Melbourne, Melbourne (AU)

( * ) Notice: Subject to any disclaimer, the term of this patent is extended or adjusted under 35 U.S.C. 154(b) by 604 days.

(21) Appl. No.: 17/444,277

(22) Filed: Aug. 2, 2021

(65) Prior Publication Data

US 2021/0364462 A1 Nov. 25, 2021

Related U.S. Application Data

(63) Continuation of application No. PCT/AU2020/050079, filed on Feb. 4, 2020.

(30) Foreign Application Priority Data

Feb. 4, 2019 (AU) .................................. 2019900329

(51) Int. Cl.
*G01N 27/22* (2006.01)
*A01G 25/16* (2006.01)
(Continued)

(52) U.S. Cl.
CPC ......... *G01N 27/223* (2013.01); *A01G 25/167* (2013.01); *G01K 1/143* (2013.01);
(Continued)

(58) Field of Classification Search
CPC .. G01N 27/223; A01G 25/167; G06F 2111/10
(Continued)

(56) References Cited

U.S. PATENT DOCUMENTS 9,519,861 B1 * 12/2016 Gates ..................... G06N 20/00
9,756,797 B2 * 9/2017 Sarver ................. A01G 25/167
(Continued)

FOREIGN PATENT DOCUMENTS

ES 2377394 A1 3/2012
WO 95/06881 A1 3/1995
WO 2018/107245 A1 6/2018

OTHER PUBLICATIONS

International Search Report issued for International Patent Application No. PCT/AU2020/050079, dated Apr. 17, 2020 in 5 pages.
(Continued)

*Primary Examiner* — Ricky Go
(74) *Attorney, Agent, or Firm* — Knobbe, Martens, Olson & Bear, LLP

(57) ABSTRACT

A method of calculating a soil moisture profile includes obtaining a capacitance measurement of a soil surface at a location, applying a preselected calibration to the capacitance measurement to obtain a top surface moisture estimate, obtaining local climatic and hydrological data correlated with the location, the local climatic and hydrological data, which includes at least local water input data, and calculating an estimate of the soil moisture at the location by applying a preselected evapotranspiration model to the top surface moisture estimate and the local climatic and hydrological data.

20 Claims, 9 Drawing Sheets

(51) Int. Cl.
  *G01K 1/143* (2021.01)
  *G01N 33/24* (2006.01)
  *G06F 30/20* (2020.01)
  *G06F 111/10* (2020.01)

(52) U.S. Cl.
  CPC .......... *G01N 33/246* (2013.01); *G06F 30/20* (2020.01); *G06F 2111/10* (2020.01)

(58) Field of Classification Search
  USPC .......................................................... 702/2
  See application file for complete search history.

(56) References Cited

U.S. PATENT DOCUMENTS

| | | | |
|---|---|---|---|
| 2004/0145379 A1 | 7/2004 | Buss | |
| 2008/0091307 A1* | 4/2008 | Dansereau | G01W 1/02 700/284 |
| 2018/0348714 A1* | 12/2018 | Larue | A01G 25/092 |
| 2018/0368339 A1* | 12/2018 | van der Lee | A01G 25/167 |
| 2020/0110170 A1* | 4/2020 | Chandra | G01S 13/88 |

OTHER PUBLICATIONS

Allen et al., "Crop evapotranspiration—Guidelines for computing crop water requirements"; FAO Irrigation and drainage paper 56, Rome (1998).

Wigneron et al., "Estimating root zone soil moisture from surface soil moisture data adn soil-vegetation-atomosphere transfer modeling"; Water Recourses Research, vol. 35, No. 12, pp. 3735-3745, Dec. 1999.

Gorr, "Neural networks in forecasting: Special section Research prospective on neural network forecasting"; International Journal of Forecasting 10; pp. 1-4 (1994).

Kaastra et al., "Designing a neural network for forecasting financial and economic time series"; Neurocomputing 10; pp. 215-236 (1996).

Moré, "The Levenberg-Marquardt Algorithm: Implementation and Theory"; Work performed under hte auspices of the U.S. Energy Research and Development Administration; pp. 105-116 (1977).

Zhang, "Time series forecasting using a hybrid ARIMA and neural network model"; Neurocomputing 50, pp. 159-175 (2003).

Zhang et al., "Neural network forecasting for seasonal and trend time series"; Computing, Artificial Intelligence and Information Technology; European Journal of Operational Research 160, pp. 501-514 (2005).

* cited by examiner

SOIL MOISTURE ESTIMATION

CROSS-REFERENCE TO RELATED APPLICATIONS

The is a continuation of International Application No. PCT/AU2020/050079 filed on Feb. 4, 2020, which claims a priority to Australian Patent Application No. 2019900329. The entire disclosure of these applications are incorporated by reference herein.

FIELD OF THE INVENTION

The invention generally relates to estimating soil moisture.

BACKGROUND TO THE INVENTION

Soil water content is a parameter with implications in an array of engineering, hydrology, climate science, water resource management, remote sensing and agricultural applications. The challenge of increasing water use in agriculture, which is known to be the largest consumer of water resources, can be alleviated by better-informed irrigation decisions and smart farming systems that are based on accurate measurements of soil water content. In addition, accurate and rapid measurements of soil water content can enhance site assessments in a broad range of civil engineering applications such as road construction, since the soil moisture is an important parameter to derive the strength and the integrity of the infrastructure. Furthermore, in bushfire management, the fuel availability estimates used for issuing warnings are partly based on the soil moisture deficit.

Soil water content can be directly measured using the oven drying method which is accurate and inexpensive; however, it is time-consuming and labour-intensive. In addition, there are indirect techniques which utilise other soil parameters as a proxy to estimate soil water content. Neutron probes are commonly used for these indirect techniques; however, there are limitations associated with their use. These limitations are primarily due to the probes containing radioactive materials and include the high cost of equipment, the requirement of a certificate to operate, the inability to use as a continuous monitoring tool and unreliability to estimate near surface soil water content. Furthermore, the common methods of measuring soil water content often cannot provide immediate feedback.

SUMMARY OF THE INVENTION

According to an aspect of the present invention, there is provided a method of calculating a soil moisture profile, comprising the steps of: obtaining a capacitance measurement of a soil surface at a location; applying a preselected calibration to the capacitance measurement to obtain a top surface moisture estimate; obtaining local climatic and hydrological data correlated with the location, the local climatic and hydrological data comprising at least local water input data; and calculating an estimate of the soil moisture at the location by applying a preselected evapotranspiration model to the top surface moisture estimate and the local climatic and hydrological data.

The evapotranspiration model may comprise inputting the top surface moisture estimate and its variation over time t into an algorithm having the form:

$$\frac{\partial \theta_{surface}}{\partial t} = B/(\rho_W d_1)(P_G - E_G) - B_2/\tau_1(\theta_{surface} - \theta_{depth})$$

for $0 \leq \theta_{surface} \leq \theta_{Sat}$ $$\frac{\partial \theta_{depth}}{\partial t} = B_2/(\rho_w d_2)(P_G - E_G - E_{TR}) - B_3/\tau_1 \max[0, (\theta_{depth} - \theta_{FC})]$$

for $0 \leq \theta_{depth} \leq \theta_{Sat}$ where θ denotes soil moisture, $\rho_w$ is the density of water, $d_1$ is the depth of the surface soil, $d_2$ is the depth of interest corresponding to the desired soil moisture profile, $P_G$ is an input due to rainfall and irrigation, which is obtained from obtained climatic and hydrological data, $E_G$ is the soil evaporation and $E_{TR}$ represents the transpiration rates, $\tau_1$ is a restore constant for one day, and $B_1$, $B_2$ and $B_3$ are site specific parameters related to the particular soil type, and $\theta_{FC}$ is the field capacity of the soil which must be determined based on empirical testing.

The evapotranspiration model may be a transient multiplayer soil moisture simulation model. Optionally, the transient multiplayer soil moisture simulation model is based on the FOA56 algorithm, for example of the form:

$$ET_0^{(P-M)} = ET_{rad}^{(P-M)} + ET_{aero}^{(P-M)} = \left\{\frac{0.408\Delta(R_n - G)}{\Delta + \gamma(1 + 0.34u)}\right\} + \left\{\frac{900\gamma}{[\Delta + \gamma(1 + 0.34u)]} \cdot \frac{uD}{(T + 273)}\right\}$$

where the term $ET_{rad}^{(P-M)}$ is the radiation term of the FAO-56 Penman-Monteith equation, and $ET_{aero}^{(P-M)}$ is the aerodynamic component, $R_n$ is the net radiation at the surface (MJ·m$^{-2}$·d$^{-1}$); Δ is the slope of the saturation vapor pressure curve (kPa/° C.); γ is psychrometric coefficient (kPa/° C.); G is soil heat flux density (MJ·m$^{-2}$·d$^{-1}$) and u is wind speed at 2 m height (m·s$^{-1}$).

According to another aspect of the present invention, there is provided a method of calculating a soil moisture profile, comprising the steps of: obtaining a capacitance measurement of a soil surface at a first location; applying a preselected calibration to the capacitance measurement to obtain a top surface moisture estimate; obtaining at least one direct measurement from corresponding at least one soil moisture probe at a different location; and calculating an estimate of the soil moisture profile at the first location by applying a preselected model to the top surface moisture estimate and the at least one direct measurement.

The preselected model may be based on a machine learning algorithm, such as one that takes the form:

$$f(y_{t-1}, y_{t-2}, \ldots, x_{t-1}, x_{t-2}, \ldots)$$

According to another aspect of the present invention, there is provided a method of calculating a soil moisture profile, comprising the steps of: obtaining a capacitance measurement of a soil surface at a location; applying a preselected conversion to the capacitance measurement to obtain a top surface moisture estimate; obtaining external data; and calculating an estimate of the soil moisture at the location by applying a preselected model to the top surface moisture estimate and the external data.

Optionally, the capacitance measurement is obtained by a contact sensor in contact with the soil surface, the contact sensor comprising at least one capacitor.

The method optionally further comprises obtaining a surface temperature measurement at the location, and wherein the preselected evapotranspiration model incorporates the surface temperature measurement when estimating the soil moisture at the location. The surface temperature measurement may be obtained by a temperature sensor component of the contact sensor.

The method optionally further comprises obtaining a selection of soil type from a plurality of predefined soil types, and wherein the preselected evapotranspiration model incorporates the selected soil type when estimating the soil moisture at the location. The predefined soil types may include two or more of: all soil types; clay or silty or loamy soil; and sandy soil.

The method optionally further comprises obtaining a calibration measurement being a capacitance measurement of air at the location; and modifying the capacitance measurement in accordance with the calibration measurement in order to calibrate the capacitance measurement.

Optionally, the preselected calibration comprises applying the following calculation:

$$\theta_{surface} = \alpha \cdot (C_{soil} - C_{air})^\beta$$

wherein $\theta$ is the top surface moisture estimate, $C_{soil}$ is capacitance measurement, $C_{air}$ is the capacitance of air at the location, and $\alpha$ are $\beta$ are soil specific coefficients.

The local climatic and hydrological data may be obtained from a nearest site non-specific weather station. The local climatic and hydrological data may also, or instead, be obtained from a nearest site specific weather station.

The method may be implemented by a processing device, and the method may include the processing device receiving the capacitance measurement via a data a data transfer. The processing device may be configured to receive the capacitance measurement via one or more of the following: wired data transfer; and wireless data transfer. The processing device may be configured to receive the capacitance measurement via a mobile broadband data transfer.

According to another aspect of the present invention, there is provided a contact sensor comprising a housing on which is located a sensitive region, the sensitive region defined by a capacitance sensor located at least partially within the housing, the contact sensor further comprising circuitry configured to obtain capacitance measurements from the capacitance sensor and to store said measurements within a memory.

The circuitry may be further configured to implement the method of one of the above aspects. The contact sensor may further comprise a wireless data module controllable by the circuitry and configured to receive external data. The housing may define a waterproof or water-resistant enclosure. A sensitive region of the contact sensor may be circular, optionally with a diameter of between 8 and 48 mm.

According to another aspect of the present invention, there is provided a system for calculating a soil moisture profile comprising a contact sensor according to the above aspect and processing means for implementing the method of any of the above aspects.

As used herein, the word "comprise" or variations such as "comprises" or "comprising" is used in an inclusive sense, i.e. to specify the presence of the stated features but not to preclude the presence or addition of further features in various embodiments of the invention.

BRIEF DESCRIPTION OF THE DRAWINGS

In order that the invention may be more clearly understood, embodiments will now be described, by way of example, with reference to the accompanying drawing, in which.

DESCRIPTION OF EMBODIMENTS

Figure 1:
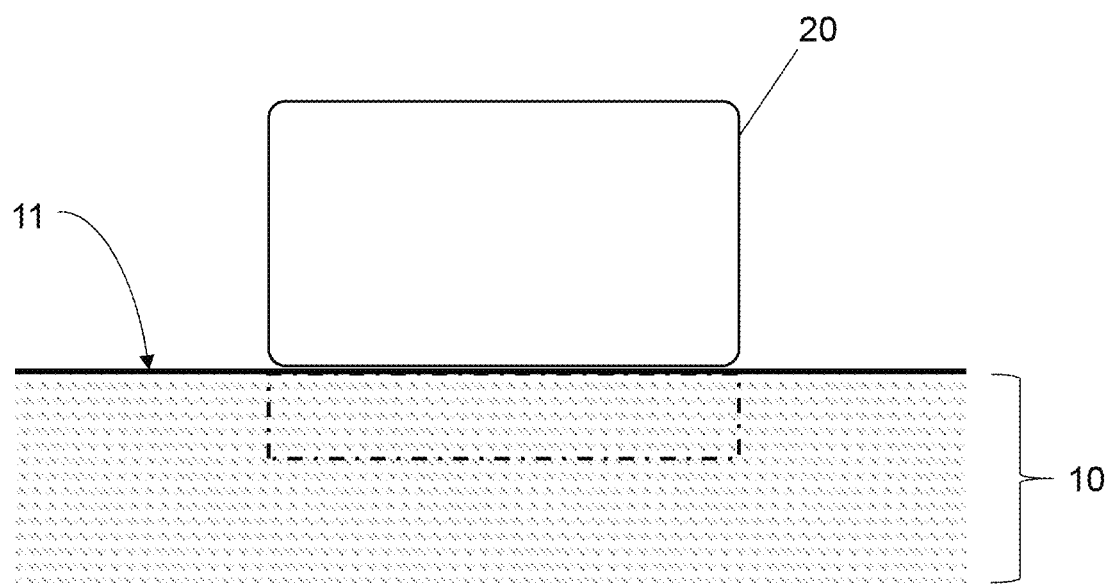
FIG. 1 shows a contact device according to an embodiment placed onto a soil surface.

FIG. 1 shows a contact sensor 20 placed into contact with a top surface 11 of a volume of soil 10. As can be seen, the volume of soil 10 is generally a portion of a large continuous volume which extends in three dimensions—relevantly, the particular volume of the soil 10 is defined by the sensing capabilities of the contact sensor 20 and the particular location of the contact sensor 20.

Figure 2:
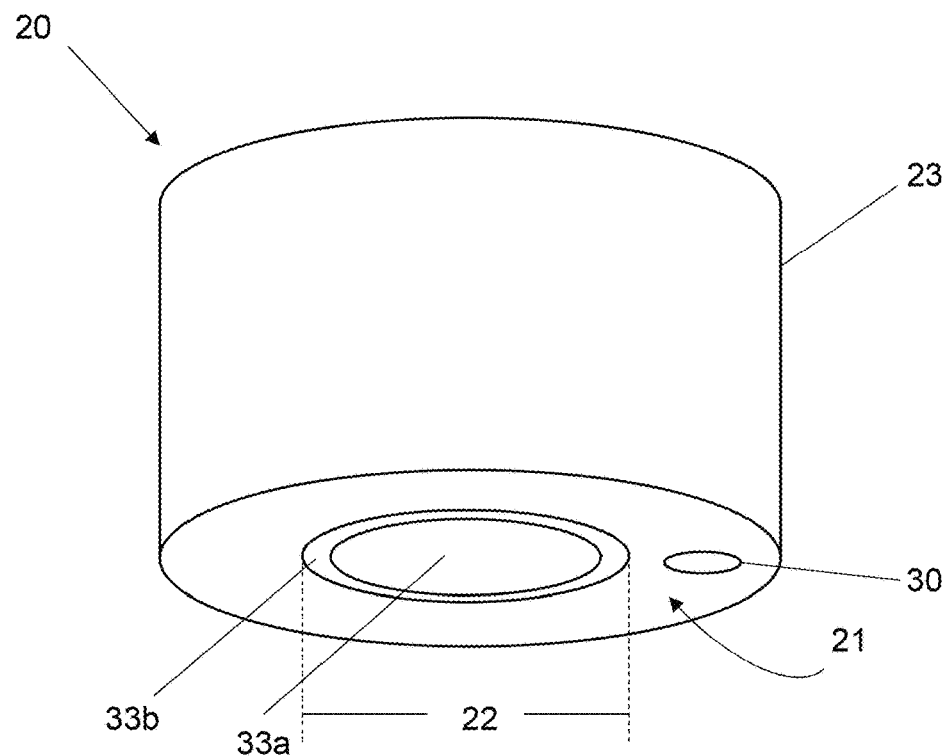
FIG. 2 shows a view of a contact device according to an embodiment.
Figure 3:
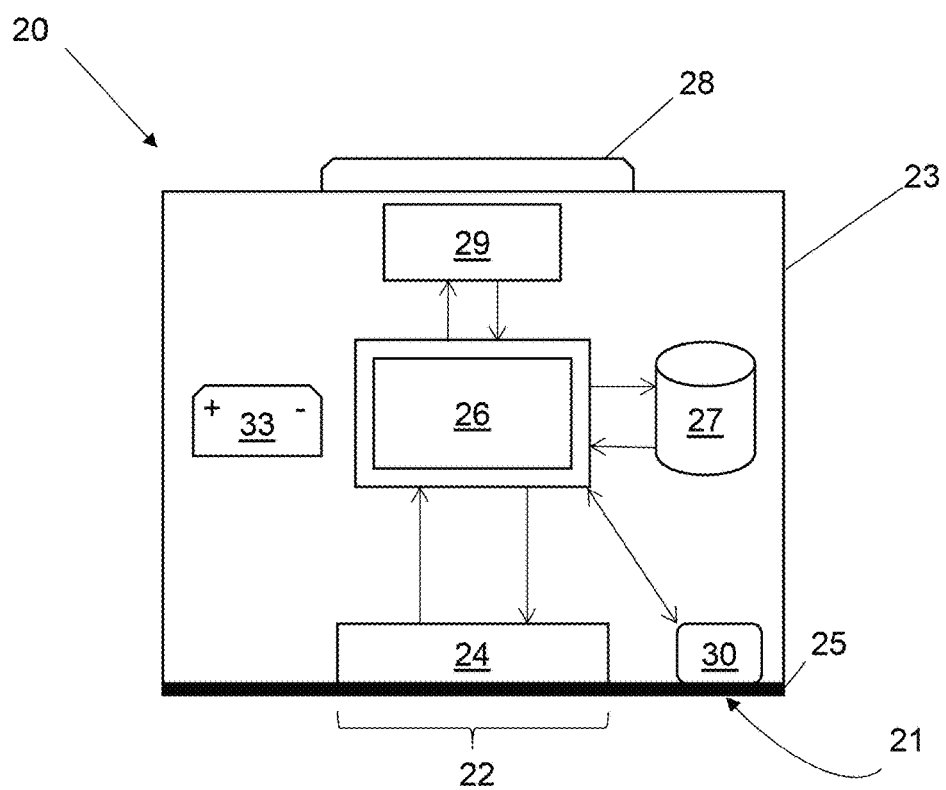
FIG. 3 shows a schematic cross-sectional view of the contact device of FIG. 2.

FIG. 2 shows an embodiment of the contact sensor 20 having a housing 23 of roughly cylindrical shape including a circular sensing surface 21. However, other shapes can be utilised, preferably such that the housing 23 defines a waterproof or water-resistant enclosure. FIG. 3 shows a cross-sectional side view of the contact sensor 20. A sensitive region 22 is located within the sensing surface 21. The housing 23 comprises a capacitance sensor 24 which can either include a surface corresponding to the sensitive region 22 or can include a surface coupled to the sensitive region 22 (e.g. in the latter case as shown in the figure, where a protective and/or waterproof barrier 25 is utilised). As shown in FIG. 3, the capacitance sensor 24 is electrically interfaced with circuitry 26. The circuitry 26 is configured such as to enable the contact sensor 20 to make a capacitance measurement via the sensitive region 22 and to store capacitance measurements within a memory 27. Optionally, the contact sensor 20 comprises a display 28 (e.g. a LCD display) configured to display information in respect to instructions received from the circuitry 26. The contact sensor 20 typically comprises a battery 33 although it is anticipated that the contact sensor 20 can be powered from an external power source.

The circuitry 26 can take different forms depending on the embodiment. In one example, the circuitry 26 comprises a microcontroller having a processor, a memory, and input and output ports. In another example, the circuitry 26 comprises a microprocessor (or multiple microprocessors) interfaced with a memory and an input/output module. In other examples, the circuitry 26 comprises a programmable logic controller, a field-programmable gate array, or specialised discrete circuitry. In an embodiment, the memory 27 comprises a non-volatile memory, such as a FLASH memory or EEPROM memory. In an implantation, the memory 27 may include a removeable memory. The memory 27 can also comprise a volatile memory.

In an embodiment, the sensitive region 22 of the contact sensor 20 is circular and has a diameter between 8 and 48 mm. A larger surface area of the sensitive region 22 provides for improved sensitivity, however, as a trade-off a larger surface area can lead to inconsistent surface contact with the top surface 11 due to undulations of the top surface 11. In the embodiment shown in FIG. 2, the sensitive region 22 comprises two electrodes 32, 33 of the capacitance sensor 24. The first electrode 32 defining a circular area surrounded by the annular ring of the second electrode 23. In an embodiment, the diameter of the first electrode 32 is between 7 and 42 mm and the width of the second electrode 33 is between 1 and 6 mm. In an alternative embodiment, the contact sensor 20 can comprise more than one pair of electrodes 32 (not shown). Also, in an alternative, the sensitive region 22 is not circular. The contact device 20 may also comprise a temperature sensor 30 which can be utilised to obtain local temperature measurements commensurate with the capacitance measurements—these may be utilised by some models described below.

In an embodiment, the contact sensor 20 comprises a wireless data module 29 interfaced with the circuitry 26. The wireless data module 29 may be configured for relatively local wireless data communication (e.g. Bluetooth, WiFi, ZigBee, etc.) where the communication is over a distance of, for example, approximately 100 metres or less. Alternatively, or in addition, the wireless data module 29 may be configured for wide area data communication (e.g. 3G mobile broadband such as UMTS, CDMA2000, EDGE, W-CDMA, HSPA, etc. or 4G mobile broadband such as LTE). In one embodiment, the wireless data module 29 includes a long-range data transmission such as LoRa.

In an embodiment, the circuitry 26 of the contact sensor 20 is configured for processing capacitance measurements made by the capacitance sensor 24. In this embodiment, the circuitry 26 is configured to implement processing functionality and the memory 27 typically comprises programming instructions configured to cause the circuitry to implement the relevant processing steps descried herein. The circuitry 26 is configured to receive external data from at least one external data source. For embodiments utilising the wireless data module 29, the external data can be received via the wireless data module 29. Therefore, the wireless data module 29 is configured for wireless data communication with one or more external data source(s). The external data can also (or alternatively) be received via a user input. In another example, a non-volatile memory (e.g. a SD Card) can be provided comprising the external data, and the circuitry 26 can then read the data from the non-volatile memory. It is also envisaged that the external data can be provided via a wired data transfer (e.g. RS 232, USB, ethernet, or any other suitable protocol).

In another embodiment, the processing of the capacitance measurements occurs at a processing server which is logically and physically distinct from the contact sensor 20. The capacitance measurements may be stored in the memory 27 and subsequently communicated to the processing server. Alternatively, or in addition, the capacitance measurements may be immediately communicated to the processing server. The contact sensor 20 can comprise the wireless data module 29 previously described configured to communicate the capacitance measurements to the processing server. Alternatively, or in addition, the memory 27 comprises a removeable non-volatile memory which is removed and subsequently interfaced with the processing server 25 in order to effect communication of the capacitance measurements. The processing server is configured to receive external data from at least one external data source. The external data will typically be communicated via a digital communications network such as the Internet, although it is envisaged that private intranets may be utilised.

Depending on the embodiment, the contact sensor 20 or the processing server 31 comprises a user interface for enabling a user to provide inputs as discussed herein. For example, the user can be enabled to select a soil type being measured. Generally, the user interface can be of a known type—for example, the contact sensor 20 may be provided with a touch screen interface, one or more buttons/switches/etc. In another example, the processing server 31 can receive inputs from a separate computing device (e.g. a user's laptop or desktop computer) or directly via a touchscreen, keyboard and mouse, etc.

For the purposes of the present disclosure, it is assumed that the capacitance measurements obtained by the contact sensor 20 are processed by suitable configured hardware (e.g. the circuitry 26 or the processing server).

Figure 4:
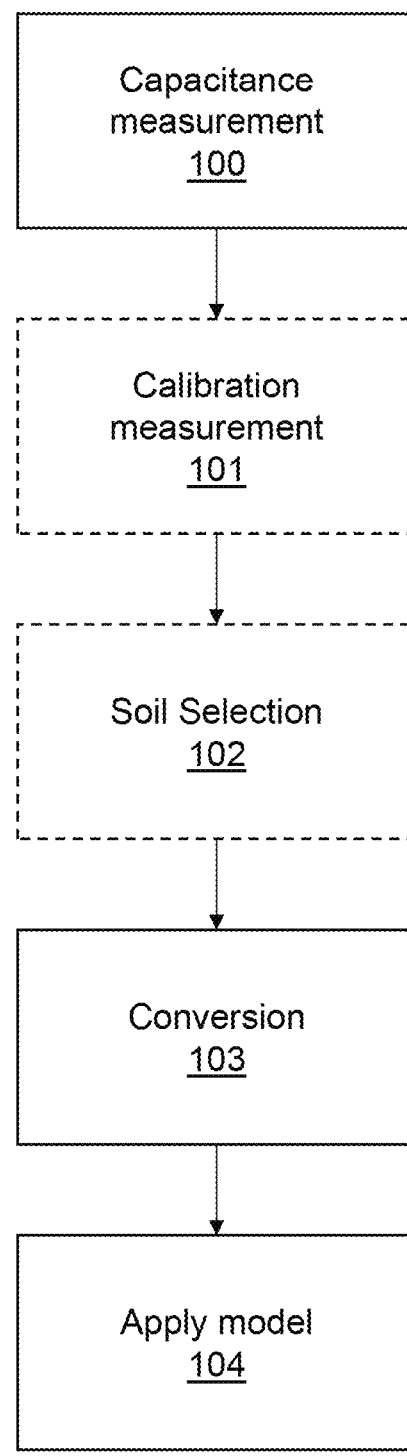
FIGS. 4-6 show methods of calculating soil moisture profile according to embodiments.

FIG. 4 shows a method for estimating a soil moisture profile at a particular location according to an embodiment. Relevantly, the method is suitable for obtaining a soil moisture profile at depths greater than that can be sensed directly by contact sensor 20. For example, the method may be suitable for obtaining a soil moisture profile for depths of 1 metre or more, whereas the contact sensor 20 may be suitable for direct measurements of 10 cm or less, such as within 5 cm of the soil surface. In some embodiments, it is expected that the direct measurement will be applicable to a depth of approximately 2 cm. A soil moisture profile corresponds to information as the water content of a soil 10 at a particular depth or down to a particular depth.

Capacitance measurement step 100 comprises obtaining a capacitance measurement of a volume of the soil 10. For example, the contact sensor 20 can be placed into contact with the top surface 11 of the soil 10 such that the sensing surface 21 is in contact with the top surface 11. A measurement of the capacitance is then made. In an embodiment, the contact sensor 20 is pressed onto the top surface 11 to ensure good contact with the top surface 11 when a capacitance measurement is required. In an implementation, the measurement may be made in response to the contact sensor 20 being pressed onto the top surface 11. In another implementation, means may be provided for a user to instruct the contact sensor 20 to make the capacitance measurement (e.g. via a button, trigger, stich, etc.). In another embodiment, the contact sensor 20 is configured to remain at the same location for an extended period of time. In an embodiment, the contact sensor 20 is configured to make a capacitance measurement in response to receiving a command from an external data source. In an embodiment, the contact sensor 20 is configured to make a capacitance measurement periodically (e.g. at predetermined intervals).

It is envisaged that several capacitance measurements may be made in the same general proximity but slightly separated—that is, at the same location with a small variance. These capacitance measurements can then be combined (e.g. averaged) in order to obtain the capacitance measurement utilised in the following steps.

Optionally, as shown in FIG. 4, the method comprises a calibration measurement step 101—this may be required for the preselected conversion model. For example, the calibration measurement step 101 may comprise utilising the contact sensor 20 to make a capacitance measurement of the air above the top surface 11.

The capacitance measurement is then converted into a top surface soil moisture estimate ($\theta_{surface}$), at conversion step 103. The top surface soil moisture estimate is an estimate of the moisture present within the volume of the soil 10 as defined in FIG. 1 (i.e. that which can be sensed by the contact sensor 20). The conversion step 103 is typically implemented by the processor of the relevant embodiment. Therefore, the conversion step 103 is implemented by the contact device 20 or the processing server 31, depending on the embodiment. A predefined conversion model is utilised to implement conversion step 103. In a general sense, the conversion model is configured to determine a sufficiently accurate estimation of the top surface moisture (that is, the moisture level within the detection range of the capacitance sensor 24) based on the measure capacitance. The conversion model may also take one or more additional inputs, for example, a user may be requested to select a soil type from a plurality of preconfigured soil types.

In an embodiment, the preselected conversion model is of the form:

$$\theta_{surface} = \alpha \cdot (C_{soil} - C_{air})^\beta \tag{1}$$

wherein $\theta_{surface}$ is the top surface moisture estimate, $C_{soil}$ is capacitance measurement, $C_{air}$ is the capacitance of air at the location, and $\alpha$ are $\beta$ are soil specific coefficients. Accordingly, use of this model requires undertaking optional step 101 as it requires a measurement of the capacitance of air at the location where the capacitance of the soil 10 was measured. For example, laboratory tests found values of $\alpha=1.14$ and $\beta=1.21$ ($R^2=0.90$, RMSE=4.95%) for sand and $\alpha=1.4$ and $\beta=1.23$ ($R^2=0.96$, RMSE=4.62%) for clay (RMSE being the root mean square error).

The soil specific coefficients are typically predetermined—for example, these coefficients are determined through empirical studies of different soil types. As shown in FIG. 4, the method may optionally comprise a soil selection step 102. Here, a user selects a soil type from a plurality of soil types stored in a memory (e.g. the memory 27 of the contact sensor 20 or the memory of the processing server 31, depending on the embodiment). Each soil type of the plurality is associated with an $\alpha$ value and a $\beta$ value, which are provided to the model after selection. In an example, the plurality of soil types includes: all soil types (i.e. parameters that may be suitable in a general sense); clay or silty or loamy soil (i.e. parameters more suitable for these soils compared to the general parameters); and sandy soil (i.e. parameters more suitable for these soils compared to the general parameters). Alternatively, preselected values for $\alpha$ and $\beta$ can be utilised—for example, where the contact sensor 20 is provided for use with a particular soil type.

Figure 8:
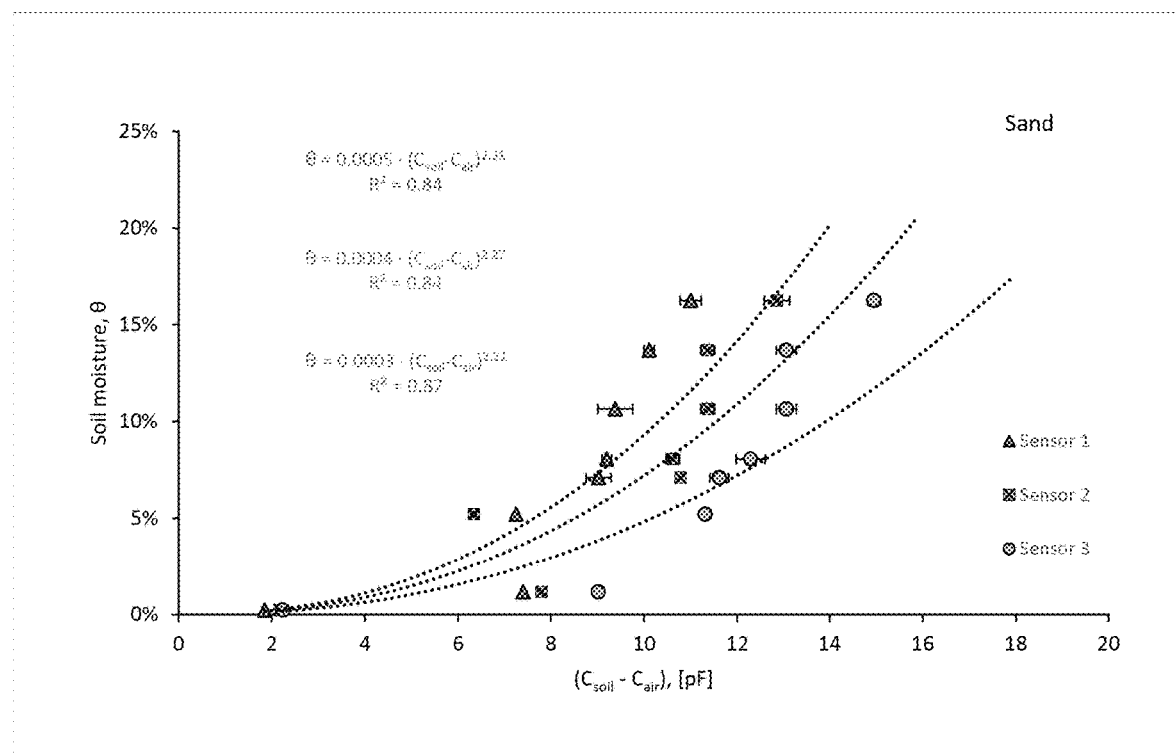
FIGS. 8 and 9 show determination of values $\alpha$ and $\beta$.
Figure 9:
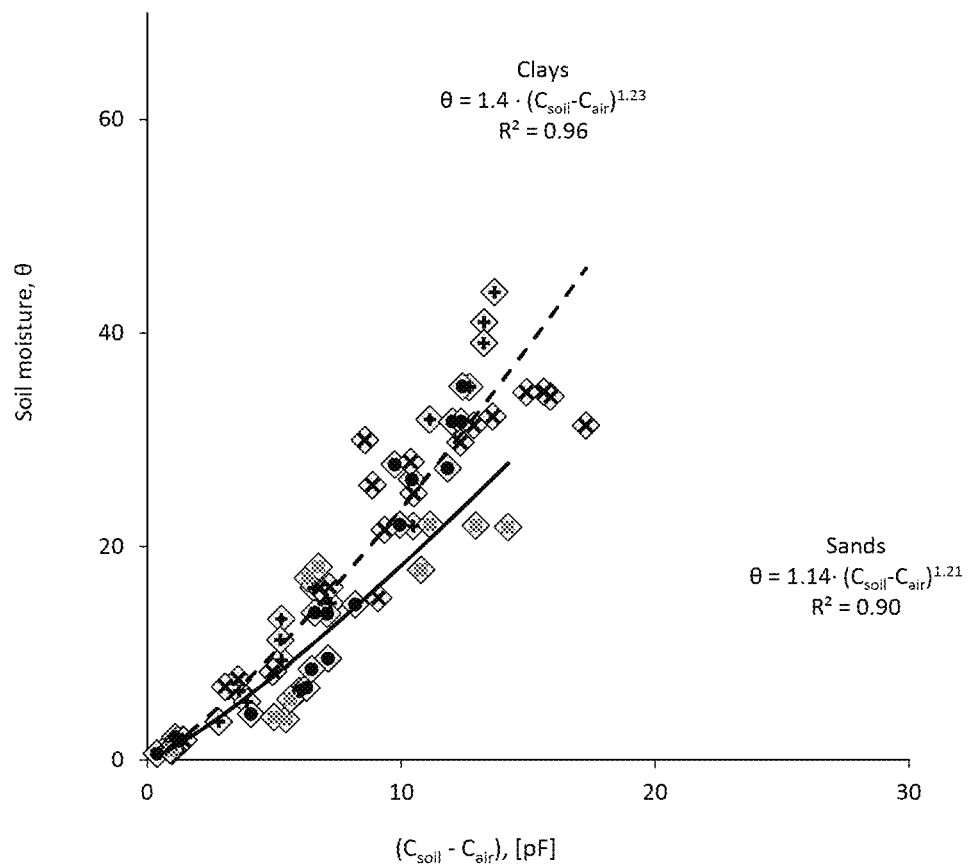

FIG. 8 shows laboratory results for determining $\alpha$ and $\beta$ for different contact devices 20 (labelled "Sensor 1", "Sensor 2", and "Sensor 3"). As can be seen, the parameters $\alpha$ and $\beta$ can be determined empirically when soil moisture is measured independently of the contact sensor 20 measurement. The determination is for a particular soil type (i.e. "sand"). Similarly, FIG. 9 shows laboratory results for determining $\alpha$ and $\beta$ for different contact devices 20 for soil type "clay".

The result of completing step 103 (and where applicable, optional steps 101 and 102) is a top surface moisture estimate that will typically be valid for a soil depth of 10 cm or less (for example, approximately 2 cm as already discussed). The particular depth may depend on factors such as soil type and temperature.

Next, the soil moisture profile is calculated through application of a predefined model, at model application step 104. The predefined model is selected based on its ability to estimate the soil moisture profile based on the top surface soil moisture estimate—therefore, its ability to estimate the soil moisture profile to a depth greater than that directly measured using the contact sensor 20. Generally, the predefined model will take external data as an input in combination with the top surface soil moisture estimate. The particular external data obtained is selected in accordance with previously obtained empirical data.

The result of step 106 can be displayed (e.g. via display 28 when available) at display step 107. The displayed indication of the soil moisture profile can be modified to provide a useful indicator to the user (e.g. by categorising the result according to one of a plurality of categories such as: dry, moderate, optimal, over-saturated).

Figure 5:
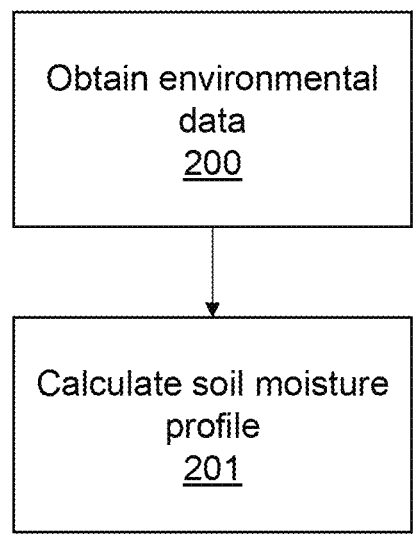

FIG. 5 shows the implementation of step 104 according to an embodiment. The method comprises obtaining local climatic and hydrological data, at environmental data step 200. The climatic and hydrological data is referred to as "local" as it is intended that the data is applicable to the location at which the capacitance measurement is made. The local climatic and hydrological data comprises at least local water input data which provides information as to the quantity of water received at the location over a period of time.

The local climatic and hydrological data can be obtained through a data communication between the weather station and the contact sensor 20 or processing server 31 (as applicable). In an alternative embodiment, a user is enabled to enter the climatic and hydrological data after having obtained it from the weather station. In another embodiment, the climatic and hydrological data is made available via a portable memory comprising the data.

The local climatic and hydrological data is then utilised as an input into the preselected model along with the top surface soil moisture estimate in order to calculate the soil moisture profile, at step 201. In an embodiment, the contact sensor 20 or processing server is configured to incorporate one or more previously calculated soil moisture profile into the preselected model when calculating a current soil moisture profile. The inclusion of such previously calculated data may be dependent on said data being available. For example, the contact sensor 20 can be configured to periodically make measurements (e.g. every 2-3 hours) at the same location, and this data is utilised for ongoing calculations of the soil moisture profile. In an implementation of this embodiment, initial soil moisture data is obtained for the desired depth at a particular location using a direct measurement technique in order to provide initial conditions for the preselected model.

In an embodiment, the preselected model utilised in the method of FIG. 5 is an evapotranspiration model. One suitable evapotranspiration model is according to Wigneron, Olioso, Calvet, & Bertuzzi, 1999, and takes the form:

$$\frac{\partial \theta_{surface}}{\partial t} = B/(\rho_w d_1)(P_G - E_G) - B_2/\tau_1(\theta_{surface} - \theta_{depth}) \tag{2}$$

for $0 \leq \theta_{surface} \leq \theta_{Sat}$ $$\frac{\partial \theta_{depth}}{\partial t} = B_2/(\rho_w d_2)(P_G - E_G - E_{TR}) - B_3/\tau_1 \max[0, (\theta_{depth} - \theta_{FC})] \tag{3}$$

for $0 \leq \theta_{depth} \leq \theta_{Sat}$ where $\theta$ denotes soil moisture, $\rho_w$ is the density of water, $d_1$ is the depth of the surface soil moisture (i.e. the depth associated with the top surface moisture estimate $\theta_{surface}$), $d_2$ is the depth of interest corresponding to the desired soil moisture profile (i.e. the depth at which a value for soil moisture is required, said value being $\theta_{depth}$). $P_G$ is an input due to rainfall and irrigation, which is obtained from obtained climatic and hydrological data. $E_G$ is the soil evaporation and $E_{TR}$ represents the transpiration rates. $\tau_1$ is a restore constant for one day. The dimensionless coefficients $B_1$, $B_2$ and $B_3$ are site specific parameters which need to be obtained for each soil type—typically, these will previously have been determined using empirical studies and may be provided as a result of a soil type selection at step 102. $w_{FC}$ is the field capacity of the soil which is determined based on the soil profile.

In another embodiment, the preselected model utilised in the method of FIG. 5 is a transient multiplayer soil moisture simulation model. Such a model considers each layer (i.e. of soil) as a bucket and a soil water balance is applied to each layer. A reference crop evapotranspiration ($ET_o^{PM}$) is calculated based on the Penman-Monteith FOA56 algorithm or methodology (Allen et al. 1998). The algorithm can take the form:

$$ET_0^{(P-M)} = ET_{rad}^{(P-M)} + ET_{aero}^{(P-M)} = \left\{\frac{0.408\Delta(R_n - G)}{\Delta + \gamma(1 + 0.34u)}\right\} + \left\{\frac{900\gamma}{[\Delta + \gamma(1 + 0.34u)]} \cdot \frac{uD}{(T + 273)}\right\} \quad (4)$$

where the term $ET_{rad}^{(P-M)}$ is the radiation term of the FAO-56 Penman-Monteith equation, and $ET_{aero}^{(P-M)}$ is the aerodynamic component, $R_n$ is the net radiation at the surface (MJ·m$^{-2}$·d$^{-1}$); $\Delta$ is the slope of the saturation vapor pressure curve (kPa/° C.); $\gamma$ is psychrometric coefficient (kPa/° C.); G is soil heat flux density (MJ·m$^{-2}$·d$^{-1}$) and u is wind speed at 2 m height (m·s$^{-1}$). The application of the FAO-56 Penman Montheith equation requires commonly measured meteorological observations (local climatic and hydrological data) e.g. maximum ($T_{max}$) and minimum ($T_{min}$) air temperatures, solar radiation, RS, maximum ($RH_{max}$) and minimum ($RH_{min}$) relative humidity, wind speed, u, as well as site details of latitude and altitude.

Reference can be made to Allen et al. 1998 (see References for citation details) to obtain an understanding of the application of the model. In a general sense, the calculation proceeds on the basis that the soil is divided into "buckets" corresponding to layers (each having a depth). The model proceeds on the basis that the top layer (i.e. including the soil surface) receives irrigation and rainfall (for example) according to the obtained local climatic and hydrological data and then subtracts root uptake from this value. Therefore, the local climatic and hydrological data, along with the top surface soil moisture estimate(s) (i.e. with reference to step 103), can be utilised to determine the initial condition for the top layer. The soil moisture for this layer is then updated. If it exceeds a "Field Capacity" (FC) the excess is flagged as the layer's ("bucket's") drainage and transferred to the immediately lower bucket. This process is repeated for all modelled buckets (e.g. down to a root depth associated with a local crop).

Figure 6:
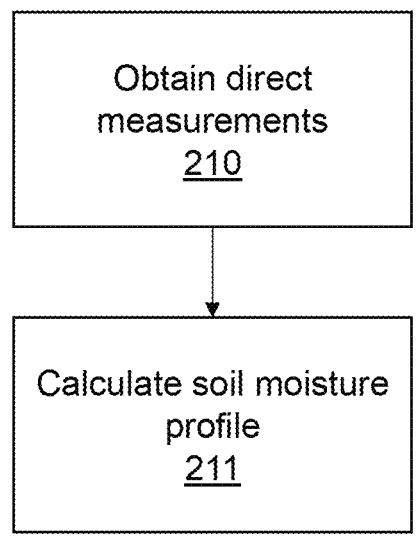
Figure 7:
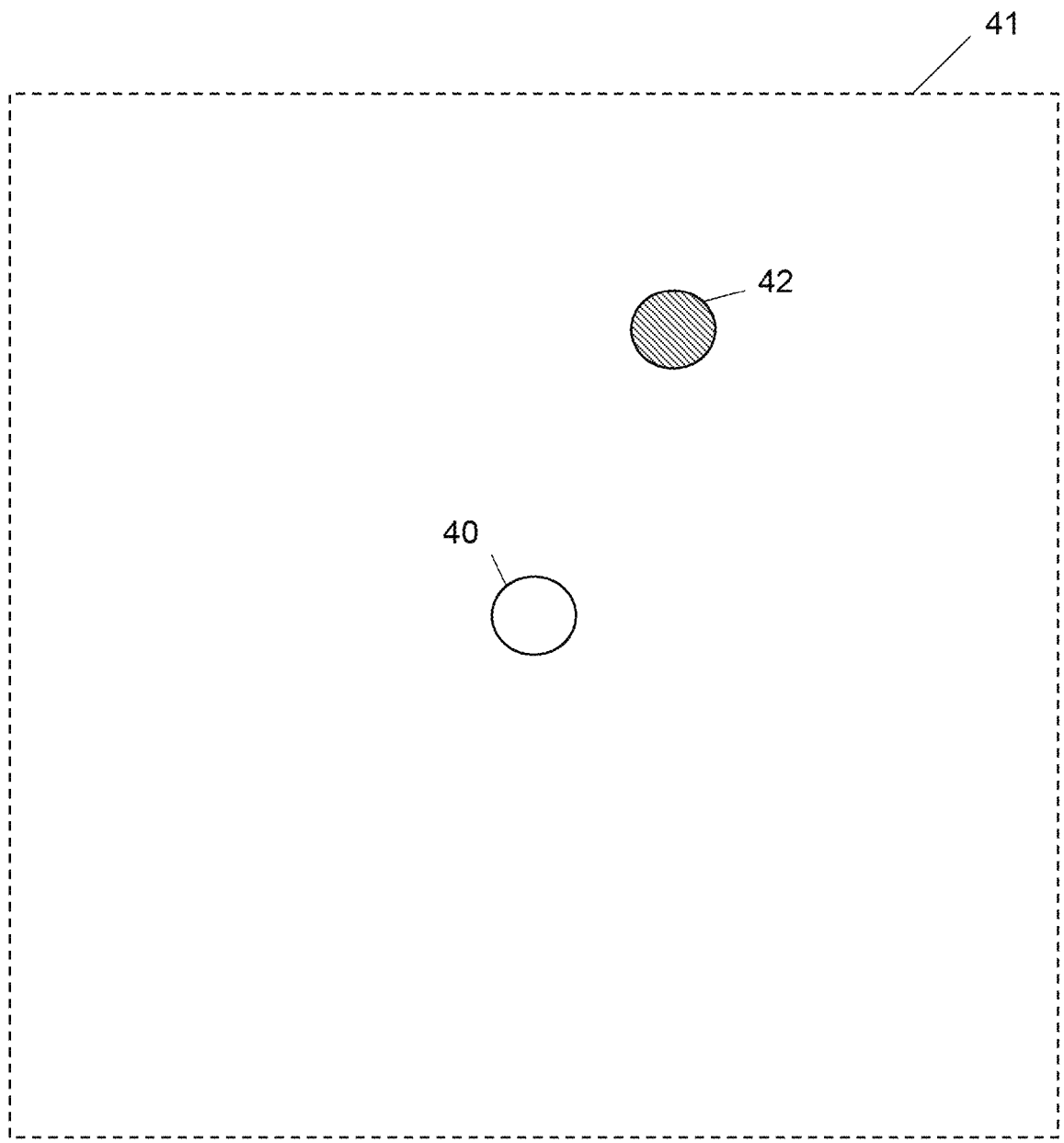
FIG. 7 shows an arrangement of direct moisture probes, according to an embodiment.

FIGS. 6 and 7 relate to another embodiment of the implementation of step 104. Referring to FIG. 7, there is shown an arrangement of a plurality of soil contact sensors 20 over a land area 41 (it is expected that one contact sensor 20 can be used in an implementation). One or more soil moisture probes 40 (one is shown in the figure) are configured for insertion into the soil 10 to a sufficient depth to obtain direct measurements of the soil moisture profile at the location of the soil moisture probe 40 (or the locations of the soil moisture probes 40). Also shown in the figure is example locations corresponding to the locations at which measurements are made using the contact sensors 20.

Referring back to FIG. 6, direct soil moisture profile measurements are taken at one or more of the soil moisture probes 40 at direct measurement step 210. These are communicated to either the contact sensor 20 or the processing server 31, depending on the embodiment. The soil moisture probes 40 may be permanently installed at a location or may be inserted and measurements made on an as-needed basis.

The method then proceeds to model application step 211. The model is selected to enable estimation of the soil moisture profile at the measurement site based on the top surface moisture estimate made at that site and the direct measurement(s) obtained at step 210. In an embodiment, the model utilises machine learning algorithms to train the model such that it can provide a useful estimation of the soil moisture profile based on the direct measurements and the top surface moisture estimate. Previous studies have found artificial neural networks to be useful for time series forecasting [Zhang and Qi, 2005]. Kaastra & Boyd, 1996; Zhang, 2003; Gorr, 1994, for example, discuss neural networks in detail. For example, a nonlinear autoregressive with exogenous input (NARX) network [Lin et al., 1996] has been found to provide useful results. The machine learning algorithm may be of the form:

$$y_t = f(y_{t-1}, y_{t-2}, \ldots, x_{t-1}, x_{t-2}, \ldots) \quad (5)$$

where $y_t$ is the neural network output at time t, which is the predicted volumetric water content ($\theta_{depth}$) at the same depths as the measured volumetric water content of the insertion probe ($\theta_{measured\_probe}$); and $x_{t-1}$ is an array of all other time-dependent variables at time (t−1), which include air temperature ($T_{air}$), surface ground temperature ($T_{ground}$), surface volumetric water content ($\theta_{surface}$) soil and crop types. Similarly, $x_{t-2}$ is an array of all other time-dependent variables at time (t−2), etc. Generally, one or more previous times can be utilised.

The model is first put through a training phase, wherein one-step-ahead forecasting is used for validating and testing the dataset. One-step-ahead forecasting is also referred to as open-loop feedback architecture, because the actual past value is used for prediction of the next time step. The Levenberg-Marquardt algorithm [More, 1997] may be used for training the dataset. Once the training is completed, the network is then switched to multi-step prediction, which is also known as a closed-loop feedback network. In the closed-loop network, each next time-step prediction is based on the previous predicted value from the network.

According to an implementation, among the data collected, 80% is used for developing the open-loop neural network. In this stage, time-dependent variables ($T_{air}$, $T_{ground}$, etc) are input x while ($\theta_{measured\_probe}$) is input y to the open-loop neural network. Once the network is constructed, the feedback loop is then closed, turning it into a closed-loop network. The remaining 20% of the input data is then used as an additional test to validate the closed-loop network. In this phase, time-dependent variables x are fed into the constructed neural network to produce ($\theta_{depth}$) at each point where the device data is collected. This output is then compared against ($\theta\_(pred-depth)$) validate the constructed closed-loop neural network.

In this way, a suitable preselected model can be created based on empirical data which is useful for calculating a soil moisture profile at an arbitrary location based on direct measurements made at small number of discrete locations.

In an embodiment, the contact sensor 20 is mounted to a vehicle which is configured to apply the contact sensor 20 to an underlying soil 10 at different locations within a geographic area. The vehicle typically will comprise a location sensor such as a GPS module to enable each acquired measurement to be associated with a particular location. These measurements can then be processed according to the methods herein to produce a series of soil moisture profiles within the geographical area.

Figure 10:
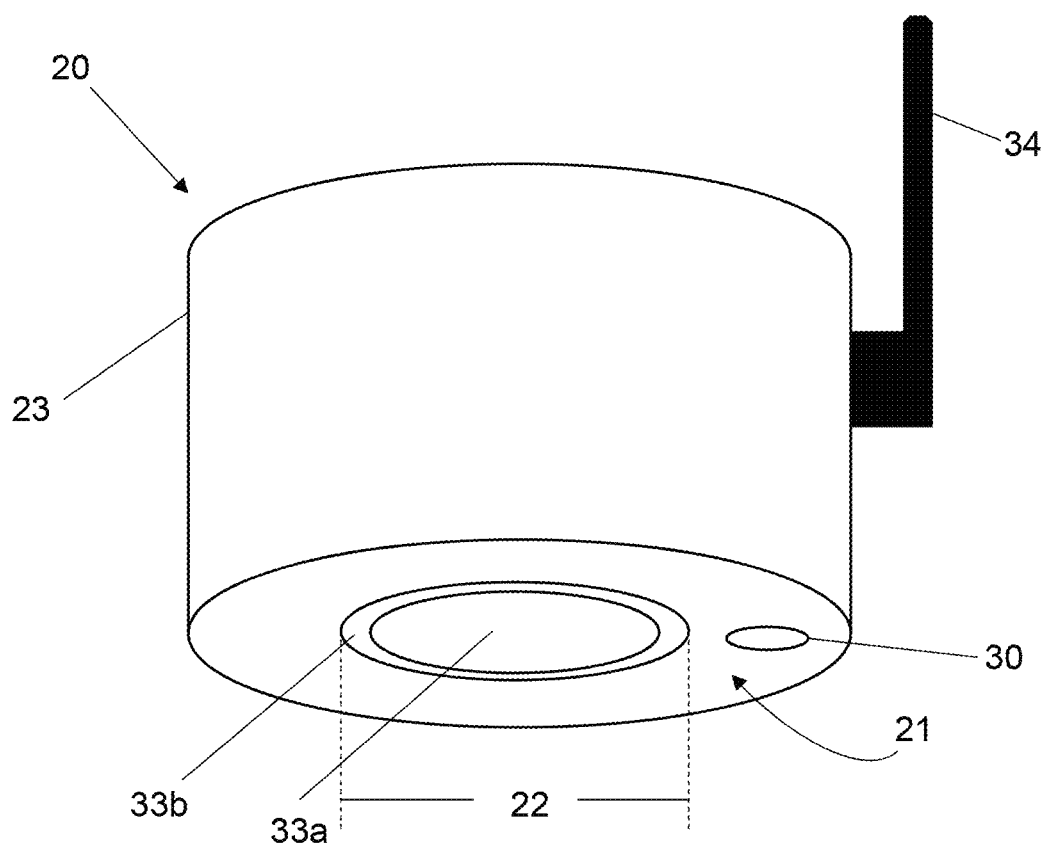
FIG. 10 shows a prototype contact device.

FIG. 10 shows the contact device 20 of FIG. 2 (i.e. with sensitive region 22 and thermometer 30) with a wireless antenna 34 extending from the housing 23. The wireless antenna 34 interfaced with the wireless data module 29 (not shown).

Further modifications can be made without departing from the spirit and scope of the specification.

REFERENCES

G. P. Zhang, M. Qi, Neural network forecasting for seasonal and trend time series, Eur. J. Oper. Res. 160 (2005) 501-514. doi:10.1016/j.ejor.2003.08.037.

I. Kaastra, M. Boyd, Designing a neural network for forecasting financial and economic time series, Neurocomputing. 10 (1996) 215-236. doi:10.1016/0925-2312(95)00039-9.

G. P. Zhang, Time series forecasting using a hybrid ARIMA and neural network model, Neurocomputing. 50 (2003) 159-175. doi:10.1016/S0925-2312(01)00702-0.

W. L. Gorr, Editorial: Research prospective on neural network forecasting, Int. J. Forecast. 10 (1994) 1-4. doi:10.1016/0169-2070(94)90044-2.

J. J. Moré, The Levenberg-Marquardt algorithm: Implementation and theory, in: Conf. Numer. Anal., Dundee, 1977: pp. 105-116. doi:10.1007/BFb0067700.

Wigneron, J. P., Olioso, A., Calvet, J. C., & Bertuzzi, P. (1999). Estimating root zone soil moisture from surface soil moisture data and soil-vegetation-atmosphere transfer modelling. Water Resources Research, 35(12), 3735-3745. doi:10.1029/1999WR900258.

Allen, R. G., Pereira, L. S., Raes D., Smith, M., 1998. Crop evapotranspiration: guidelines for computing crop water requirements. FAO Irrigation and Drainage Paper, 56, Rome, p. 300.

What is claimed is:

1. A method of calculating a soil moisture profile, comprising the steps of:
    obtaining a capacitance measurement of a soil surface obtained by a contact sensor in contact with the soil surface, the contact sensor comprising at least one capacitor at a location;
    applying a preselected calibration to the capacitance measurement to obtain a top surface moisture estimate;
    obtaining local climatic and hydrological data correlated with the location, the local climatic and hydrological data comprising at least local water input data; and
    calculating an estimate of the soil moisture at the location by applying a preselected evapotranspiration model to the top surface moisture estimate and the local climatic and hydrological data.

2. The method of claim 1, wherein the evapotranspiration model comprises inputting the top surface moisture estimate and its variation over time t into an algorithm having the form:

$$\frac{\partial \theta_{surface}}{\partial t} = B/(\rho_w d_1)(P_G - E_G) - B_2/\tau_1(\theta_{surface} - \theta_{depth})$$

for $0 \le \theta_{surface} \le \theta_{Sat}$ $$\frac{\partial \theta_{depth}}{\partial t} = B_2/(\rho_w d_2)(P_G - E_G - E_{TR}) - B_3/\tau_1 \max[0, (\theta_{depth} - \theta_{FC})]$$

for $0 \le \theta_{depth} \le \theta_{Sat}$ where $\rho_w$ is the density of water, $d_1$ is the depth of the surface soil, $d_2$ is the depth of interest corresponding to the desired soil moisture profile, $P_G$ is an input due to rainfall and irrigation, which is obtained from obtained climatic and hydrological data, $E_G$ is the soil evaporation and $E_{TR}$ represents the transpiration rates, $\tau_1$ is a restore constant for one day, and $B_1$, $B_2$ and $B_3$ are site specific parameters related to the particular soil type, and $w_{FC}$ is the field capacity of the soil which must be determined based on empirical testing.

3. The method of claim 1, wherein the evapotranspiration model is a transient multiplayer soil moisture simulation model.

4. The method of claim 3, wherein the transient multiplayer soil moisture simulation model is based on the FOA56 algorithm, for example of the form:

$$ET_0^{(P-M)} = ET_{rad}^{(P-M)} + ET_{aero}^{(P-M)} = \left\{ \frac{0.408\Delta(R_n - G)}{\Delta + \gamma(1 + 0.34u)} \right\} + \left\{ \frac{900\gamma}{[\Delta + \gamma(1 + 0.34u)]} \cdot \frac{uD}{(T + 273)} \right\}$$

where the term $ET_{rad}^{(P-M)}$ is the radiation term of the FAO-56 Penman-Monteith equation, and $ET_{aero}^{(P-M)}$ is the aerodynamic component, $R_n$ is the net radiation at the surface (MJ·m$^{-2}$·d$^{-1}$); $\Delta$ is the slope of the saturation vapor pressure curve (kPa/° C.); $\gamma$ is psychrometric coefficient (kPa/° C.); G is soil heat flux density (MJ·m$^{-2}$·d$^{-1}$) and u is wind speed at 2 m height (m·s$^{-1}$).

5. The method of claim 1, wherein the capacitance measurement is obtained by a contact sensor in contact with the soil surface, the contact sensor comprising at least one capacitor.

6. The method of claim 1, further comprising the step of:
    obtaining a surface temperature measurement at the location, and wherein the preselected evapotranspiration model incorporates the surface temperature measurement when estimating the soil moisture at the location.

7. The method of claim 6, wherein the surface temperature measurement is obtained by a temperature sensor component of the contact sensor.

8. The method of claim 1, further comprising the step of:
    obtaining a selection of soil type from a plurality of predefined soil types, and wherein the preselected evapotranspiration model incorporates the selected soil type when estimating the soil moisture at the location.

9. The method of claim 8, wherein the predefined soil types include two or more of: all soil types; clay or silty or loamy soil; and sandy soil.

10. The method of claim 1, further comprising the steps of:
    obtaining a calibration measurement being a capacitance measurement of air at the location;
    modifying the capacitance measurement in accordance with the calibration measurement in order to calibrate the capacitance measurement.

11. The method of claim 1, wherein the preselected calibration comprises applying the following calculation:

$$\theta_{surface} = \alpha \cdot (C_{soil} - C_{air})^\beta$$

wherein $\theta$ is the top surface moisture estimate, $C_{soil}$ is capacitance measurement, $C_{air}$ is the capacitance of air at the location, and $\alpha$ are $\beta$ are soil specific coefficients.

12. The method of claim 1, wherein the local climatic and hydrological data are obtained, at least in part, from a local site non-specific weather station.

13. The method of claim 1, wherein the local climatic and hydrological data are obtained, at least in part, from a local site specific weather station.

14. The method of claim 1, wherein the method is implemented by a processing device, and the method include the processing device receiving the capacitance measurement via a data a data transfer.

15. The method of claim 14, wherein the processing device is configured to receive the capacitance measurement via one or more of the following: wired data transfer; mobile broadband data transfer; and wireless data transfer.

16. A contact sensor comprising a housing on which is located a sensitive region, the sensitive region defined by a capacitance sensor located at least partially within the housing, the contact sensor further comprising circuitry configured to obtain capacitance measurements from the capacitance sensor and to store said measurements within a memory, wherein the circuitry is further configured to implement the method of claim 1.

17. The contact sensor of claim 16, wherein a sensitive region of the contact sensor is circular with a diameter of between 8 and 48 mm.

18. The method of claim 1, wherein the evapotranspiration model is a model trained with a machine learning algorithm.

19. The method of claim 18, wherein the machine learning algorithm is an artificial neural network.

20. The method of claim 18, wherein the evapotranspiration model is trained using an open-loop feedback architecture.

* * * * *